United States Patent [19]

Strohmeier

[11] Patent Number: 4,939,943
[45] Date of Patent: Jul. 10, 1990

[54] SAMPLE INJECTOR FOR A LIQUID CHROMATOGRAPH

[75] Inventor: Fred Strohmeier, Rheinmuenster, Fed. Rep. of Germany

[73] Assignee: Hewlett-Packard Company, Palo Alto, Calif.

[21] Appl. No.: 305,888

[22] Filed: Feb. 2, 1989

[30] Foreign Application Priority Data

Feb. 11, 1988 [EP] European Pat. Off. ............ 88102007

[51] Int. Cl.⁵ .............................................. B01L 3/02
[52] U.S. Cl. .................................................. 73/864.21
[58] Field of Search .................... 73/864.21–864.24, 73/864.81, 864.83, 864.84, 864.86, 864.87; 422/62, 70, 81, 82, 89, 100

[56] References Cited

U.S. PATENT DOCUMENTS

| | | | |
|---|---|---|---|
| 3,401,564 | 9/1968 | Hrdina | 73/864.21 |
| 3,831,618 | 8/1974 | Liston | 73/864.22 |
| 4,476,734 | 10/1984 | Banks et al. | 73/864.21 |
| 4,713,974 | 12/1987 | Stone | 73/864.23 |

FOREIGN PATENT DOCUMENTS 0063443  4/1985  Japan ................................ 73/864.21

Primary Examiner—Robert Raevis

[57] ABSTRACT

A sample injector for a liquid chromatograph comprises a high pressure syringe unit, a sample intake unit having a needle which can be introduced into a sample container as well as into a seat, and a 6/2-way valve. The high pressure syringe unit is designed as a piston pump with a pump head and a piston which is driven by a motor via a drive mechanism. Pressurized liquid from a solvent delivery system (SDS) can enter the pump head through an inlet port and flow along the piston to an outlet port. When sample is to be injected into a chromatographic column, the 6/2-way vale is first switched to a position dotted whereby the pressurized solvent is shunted from the high pressure syringe unit to the column. The needle is then introduced into the container and the piston (5) is retracted to a position which draws in the desired volume of sample. Thereafter, the valve is switched back to its original position so that solvent delivered from the solvent delivery system passes through the high pressure syringe unit and can transport the sample to the column. Since the solvent flushes the entire syringe unit, it is ensured that no sample residues remain in the syringe unit which would otherwise impair the chromatographic measuring process.

12 Claims, 1 Drawing Sheet

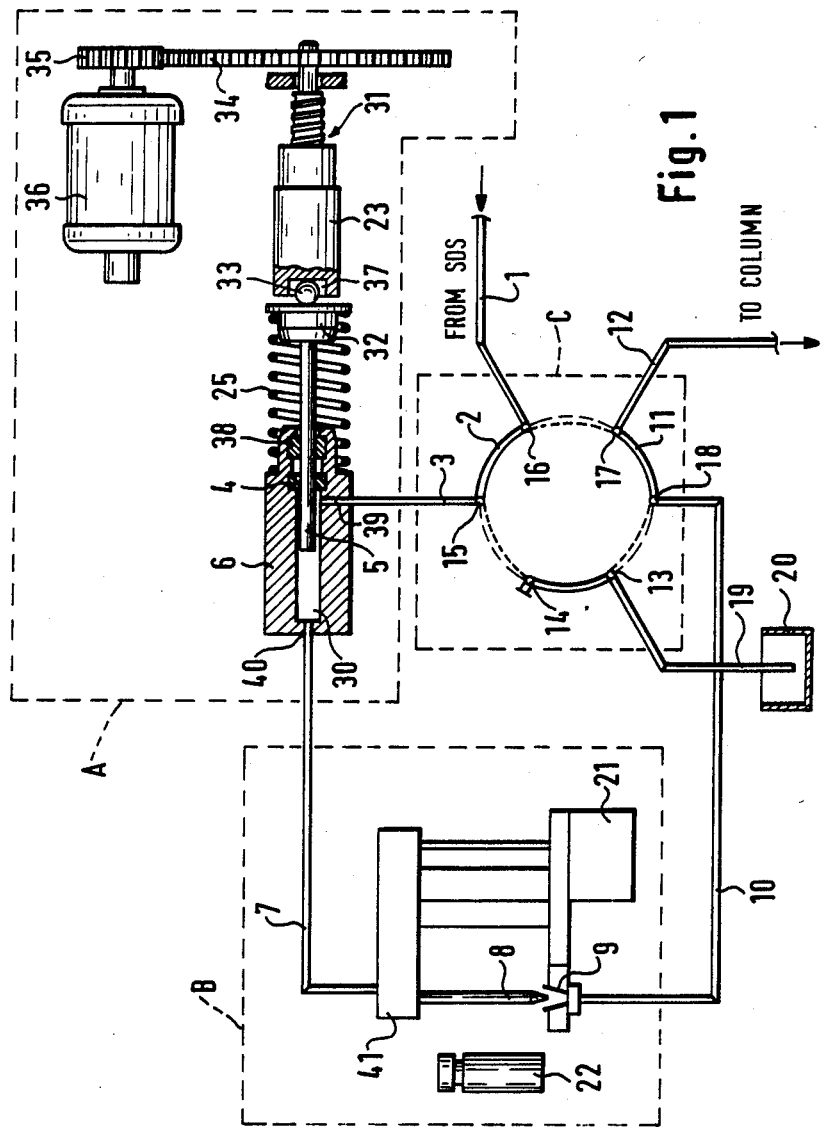

SAMPLE INJECTOR FOR A LIQUID CHROMATOGRAPH

BACKGROUND OF THE INVENTION

The invention relates to a sample injector for a liquid chromatograph. Such injectors are used for injecting the sample to be chromatographically separated into the chromatographic column.

Know injection systems typically comprise an injection loop which can be connected to the chromatographic system, i.e., the solvent delivery system and the chromatographic column, by one or several valves, and through which solvent flows at high pressure when no sample is injected. When sample is to be injected, the injection loop is uncoupled from the chromatographic system, one end of the loop is connected to a low-pressure metering syringe, and the other end is connected to a sample-intake arrangement which is moved such that it dips into a sample container. Then, the low pressure metering syringe is operated such that a desired amount of sample is drawn from the sample container into the injection loop. Once the sample is drawn in, the injection loop is switched back into the chromatographic system by means of the above-mentioned valves. The stream of solvent from the solvent delivery system then compresses the sample and transports it to the column.

With such known injection systems, air bubbles may arise in the injection system by small leakages or by degassing of the liquid in the injection system. Such air bubbles distort the separation process and therefore have a negative influence on the accuracy of measurements of sample components emerging from the column. Furthermore, if the original solvent is followed by a second solvent that turns out to be incompatible, e.g., mixing, reaction with the sample, this may lead to a loss of the sample or to variations in reproducibility. Such problems can be reduced by providing additional flushing circuits, but this increases the complexity of the injection system, leading to increased cost and decreased reliability. Furthermore, the addition of flushing circuits increases the dead volume leading to a deterioration of the chromatographic measuring accuracy.

An injection system having such an additional flushing circuit is known from the article "Automatic Liquid Chromatograph Injection and Sampling", Hewlett-Packard Journal, April 1984, pages 21-24. This known injection system comprises an additional flushing valve which permits flushing of the metering syringe and associated capillaries before each new injection of sample.

Relative to this prior art, it is an object of the invention to provide a sample injector which has a simpler design and which permits performance of repetitive injections in a simpler manner without suffering from the above-mentioned problems of known injectors.

SUMMARY OF THE INVENTION

According to an underlying principle of the invention, the metering means for drawing in the sample, for example a syringe, is coupled to the conduit system through which liquid is pumped under high pressure to the chromatographic column, in contrast to prior art injectors which are arranged in a bypass configuration relative to said conduit system. According to the invention, it is thus ensured that the metering means is permanently flushed by solvent, except for the time intervals when sample is drawn in. Consequently, the above-mentioned problems, e.g., bubble formation or accumulation of unwanted residues, are avoided without requiring extra flushing circuits and flushing procedures. Thus, the injector according to the invention has a less complex and therefore more reliable design. Since no additional flushing procedures are required, the duration of an injection cycle is reduced as compared to known injectors. The chromatographic separation time is thus reduced.

It is a further advantage of an injector according to the invention that it has only a small dead volume resulting in an increased metering accuracy.

According to a preferred embodiment of the invention, the metering means is designed like a piston pump with a pump head and a piston Which is movable within an inner bore of the pump head. The dimensions of the piston and of the inner bore of the pump head are selected such that there is a ring gap in which liquid can flow from an inlet port of the metering means to an outlet port thereof. In the normal mode, when no sample is to be drawn in from a sample container, the inlet port of the metering means is connected to the solvent delivery system of the liquid chromatograph so that solvent is delivered at high pressure through the ring gap to a sample needle. In the loading mode, when sample is to be taken in, the connection to the high pressure solvent delivery system is interrupted, the sample needle dips into a container with the sample, and the piston is retracted until the desired amount of sample is drawn in. Then, in the injection mode, the connection to the solvent delivery system is reestablished so that the pressurized solvent transports the sample to the column.

The establishing and interrupting of connections to the solvent delivery system can be accomplished by means of a 6/2-way valve which has the advantage of being a comparatively simple component that is readily available.

The transmission of the driving force to the piston of the metering means can advantageously be accomplished via a ball which can move freely in a recess of an actuating element coupled to the rest of the drive means, e.g., a ball-screw drive, with the ball contacting a piston holder to which the piston is fixed. Since there is no rigid connection between the drive means and the piston, tilt of the piston can be avoided, resulting in an increased lifetime of the seal of the pump head.

BRIEF DESCRIPTION OF THE DRAWINGS

FIG. 1 shows an embodiment of the injector according to the invention.

DESCRIPTION OF THE PREFERRED EMBODIMENT

According to FIG. 1, the injector comprises three units (indicated by blocks of dotted lines): a high pressure syringe unit A, a sample intake unit B, and a 6/2-way valve unit C. At start-up the solvent is delivered from a solvent delivery system (SDS), typically comprising a high-pressure pump, via a capillary 1 to the 6/2-way valve C. Such a 6/2-way valve is a known component in liquid chromatography and is a valve having six ports and two switching states. With the switching state of the valve C shown, the solvent flows via the internal connection 2 and the capillary 3 to the high-pressure syringe unit A.

The high-pressure syringe unit A comprises a pump head 6 with an inner cylindrical bore 30 and a piston 5 which can be moved inside the bore 30. The outer diameter of the piston 5 is smaller than the diameter of the inner bore 30 by a certain amount such that liquid can flow in the ring gap between the piston 5 and the inner wall of the pump head 6. The pump head 6 is sealed off against the outside by a high pressure-tight seal 4 which prevents any liquid from leaving the inner bore 30 of the pump head 6 at the seal 4. The piston 5 is driven via a ball-screw drive 31. One end of the piston 5 is attached to a piston holder 32 and the piston holder 32 is coupled via a ball 33 and an actuator 23 to a recirculating ball spindle. Also provided is a return spring 25. The ball-screw drive 31 is coupled to a toothed gear 34 which is coupled to a second gear 35 fixed to the shaft of a drive motor 36.

The actuator 23 which is rigidly connected to the ball-screw drive 31 comprises a recess 37 for receiving the ball 33. The ball 33 is free to move in the recess 37. The ball 33 contacts the piston holder 32 connected to the piston 5. A guiding element 38 is provided for guiding the piston 5. A return spring 25 is connected at one end to the pump head 6 and at the other end to the piston holder 32. The return spring 25 forces the piston 5 away from the pump head 6 when the actuator 23 moves away from the pump head 6. When the actuator 23 moves towards the pump head 6, the ball 33 pushes against the piston holder 32 so that the piston 5 moves into the interior of the pump head 6. The driving of the piston 5 via the freely moving ball 33 in combination with the guiding element 38 ensures that the movement of the piston 5 is free of tilt, resulting in an increased lifetime of the seal 4. In the embodiment shown in FIG. 1, the pump head 6 and the piston 5 are shown to be arranged horizontally, but it is understood that a vertical or any other arrangement is also possible. It is furthermore understood that the drive of the piston 5 can be of any kind and is not limited to the embodiment shown in FIG. 1.

As shown in FIG. 1, the solvent is introduced into the high-pressure syringe unit A immediately in front of the seal 4 via a solvent inlet port 39 so that a permanent flushing of the entire bore 30 is ensured. A capillary 7 is connected at port 40 to the pump head 6 such that liquid entering the syringe through capillary 3 and solvent inlet port 39 can leave through capillary 7.

The capillary 7 is connected to the sample-intake unit B which can be of any known design. According to FIG. 1, the sample-intake unit B may comprise a needle 8 and a seat 9 into which the needle 8 is pressed when liquid is flowing toward capillary 10. The seat 9 is connected via capillary 10 to the 6/2-way valve unit C. The needle 8 can be raised or lowered with an arm 41 which is actuated by a motor 21. Also provided is an arrangement (not shown) for positioning a sample vial 22 containing the sample below the needle 8 when the needle 8 is lifted. Such an arrangement can be, for example, a rotatable platform carrying one or several sample vials. After the desired sample vial 22 has been placed below the needle 8, the needle 8 can be lowered into the sample vial 22 such that sample can be drawn in. As an alternative to the embodiment shown in FIG. 1, the raising and lowering of the needle 8 could also be accomplished pneumatically. For example, the sample-intake unit B could be the sampling unit which is described in Hewlett-Packard Journal, April 1984, pages 21-24 and which is used in the Hewlett-Packard model HP 1090A liquid chromatograph.

The seat 9 of the sample-intake unit B is connected via a capillary 10 to port 18 of the 6/2-way valve C and via the internal connection 11 within the valve C to port 17 which is connected via a capillary 12 to the chromatographic column. Also connected to the 6/2-way valve is a port 13 which leads to a waste container 20 via a capillary 19. The 6/2-way valve can be the valve which is known from Hewlett-Packard Journal, April 1984, pages 21-24 and which is used in the Hewlett-Packard model HP 1090A liquid chromatograph.

According to the arrangement of the syringe unit A, the sample intake unit B, and the valve unit C as shown in FIG. 1, it is ensured that all parts which come into contact with sample liquid are permanently flushed.

It is understood that the high-pressure syringe unit A, the sample-intake unit B and the valve unit C have associated drive and control circuits (not shown) which are connected to a common controller for automatically controlling the operation of these units in timed relation.

In the following, the operation of the injector according to FIG. 1 is described in more detail.

When an injection is initiated by an operator, the 6/2-way valve C is switched from the position depicted with solid lines in FIG. 1 to its second position indicated by dashed lines. In that position, port 14 of the valve is connected to port 15, port 13 is connected to port 18, and port 16 is connected to port 17 while the internal connections are interrupted between ports 13 and 14, 15 and 16, and 17 and 18. With these connections, solvent flows directly from the solvent delivery system SDS via capillary 1, ports 16 and 17, and capillary 12 to the chromatographic column. The metering branch of the injection system, i.e., the syringe unit A and the sample-intake unit B, is thus uncoupled from the high pressure components of the injection system, i.e. the solvent delivery system.

Immediately after the switching of the valve C into the state indicated by the dashed lines, the pressurized solvent already in the metering branch is rerouted via capillary 10, an internal connection between ports 18 and 13, and capillary 19 to the waste container 20 and the pressure drops in the metering branch. Then, the piston 5 moves to its most fully inserted position within bore 30, i.e., to the left in FIG. 1, so that the total volume of the syringe is available for drawing in sample. The piston 5 is moved to its most fully inserted position before each injection in order to provide a defined starting position before the sample aspiration step, since the position of the piston 5 after the previous sample intake step is not always the same, but depends on the volume of the aspirated sample. If, for example, the total volume of the syringe is 50 microliters and if 50 microliters have been injected in the previous injection step, the piston 5, had to move to its most fully retracted position during the aspiration of 50 microliters of sample and now has to eject 50 microliters of solvent in order to empty the syringe before new sample is drawn in.

Once this ejection step is completed, the needle 8 is lifted from the seat 9 by means of the motor 21, and the sample vial 22 is positioned below the needle 8. Then, the needle 8 is lowered into the sample vial 22 containing the sample liquid. In order to aspirate the desired volume of sample liquid, the piston 5 is retracted a corresponding distance from its most fully inserted position, i.e. it is moved to the right in FIG. 1. The movement of the piston 5 is accomplished by a corresponding rotation of the motor 36 which is transferred via gears 35, 34 and the ball-screw drive 31 into a linear motion of the actuator 23. Since the return spring 25 exerts a constant force against the piston holder 32, the piston 5 moves to the right when the actuator 23 moves to the right.

After the desired amount of sample has been drawn in and after a short holding time which serves for pressure stabilization, the needle 8 is removed from the sample vial 22. Thereafter, the sample vial 22 is removed and the needle 8 is pressed again into the seat 9 to establish a high-pressure tight connection. Then, the valve unit C is switched back into its first position illustrated in FIG. 1 by solid lines. The solvent delivered from the solvent delivery system now compresses the liquid in the metering branch and transports the sample through the capillary 7 and the needle 8, through the seat 9, the capillary 10, the port 18, the internal connection 11 in the valve unit C, and the port 17, to the chromatographic column where the sample is chromatographically separated. Thereafter, a new injection can take place in the above described manner.

It is a further advantage of the invention that it permits injection of sample volumes which are larger than the volume of the high pressure syringe A. This can be accomplished by drawing in sample through the needle 8, putting the needle 8 back in the seat 9, intermediately storing the sample in the capillary 10, then repeating the sample intake procedure before the accumulated volume of sample is transferred to the column.

According to a further advantage, the maximum volume which can be aspirated by the metering branch can easily be increased by replacing the piston 5, or the seal 4, or the capillary 7, by elements of correspondingly different dimensions.

These and other variations upon and modifications to the described embodiments are provided for by the present invention, the scope of which is limited only by the following claims.

I claim:

1. A sample injector for a liquid chromatograph comprising:
   metering means having a bore, a piston, an inlet/outlet port, and a solvent inlet port;
   an inlet/outlet conduit in liquid communication with said bore through said inlet/outlet port;
   sample intake means adapted for admitting liquid sample into said inlet/outlet conduit so that at least partially withdrawing said piston can cause said liquid sample to move along said inlet outlet conduit toward said bore;
   a discharge conduit for transferring said liquid sample to a chromatographic column, said discharge conduit being connectable to said inlet/outlet conduit; and
   solvent introduction means for introducing solvent into said bore through said solvent inlet port while said discharge conduit is connected to said inlet/outlet conduit so that said liquid sample can be transported by solvent through said inlet/outlet conduit, through said discharge conduit, and, thence, onto said chromatographic column;
   whereby said liquid sample can be drawn towards said metering means by at least partial withdrawal of said piston, and said liquid sample can be transported to said column by action of solvent while said piston is at least partially withdrawn, and whereby said metering means is flushed by solvent while said liquid sample is transported.

2. A sample injector as recited in claim 1 wherein said solvent introduction means can divert solvent flow to said column while bypassing said solvent inlet port so that solvent can be introduced onto said column without traversing said metering means;
   whereby solvent transport through said column can be maintained simultaneously with sample aspiration.

3. A sample injector as recited in claim 2 further comprising a disposal conduit connectable to said inlet/outlet conduit, said disposal conduit being in fluid communication with a waste container so that when solvent is diverted from said solvent inlet port, solvent in said bore of said metering means can be expelled by insertion of said piston and can be transported through said inlet/outlet conduit and said disposal conduit to a waste container.

4. A sample injector as recited in claim 3 wherein said inlet/outlet conduit includes a sample needle.

5. A sample injector as recited in claim 3 wherein said metering means is a pump head, said solvent intake port being located near one end of said bore and said inlet/outlet port being located near the other end of said bore such that the free end of said piston is located near said inlet/outlet port when said piston is fully inserted into said bore, the diameter of said bore being larger than the outer diameter of said piston such that liquid can flow in the gap region from said solvent inlet port to said inlet/outlet port.

6. A sample injector as recited in claim 5 further comprising a high pressure tight seal arranged close to said solvent inlet port for sealing off said bore of said pump head.

7. A sample injector as recited in claim 6 whereby said piston is driven by drive means which comprise:
   a motor;
   power transmission means coupled to said motor;
   a ball;
   an actuator having a first end and a second end, said first end coupling said actuator to said power transmission means, and said second end having a recess for receiving said ball, the diameter of said ball being such that said ball projects above said recess but can freely move inside said recess;
   a piston holder to which said piston is mounted, said piston holder having a surface for contacting said ball; and
   a return spring for exerting force on said piston in a direction away from said pump head.

8. A sample injector as recited in claim 7 wherein said sample intake means includes:
   a seat in which the tip of said needle is positioned when no liquid sample is aspirated; and
   engagement means for disengaging said sample needle from said seat and for engaging it again after the intake of said liquid sample.

9. A sample injector as recited in claim 8 wherein said solvent introduction means includes a two-way valve having a first port connected to a solvent delivery system, a second port connected to said solvent inlet port, a third port connected to said disposal conduit, a fourth port connected to said inlet/outlet conduit, and a fifth port connected to said discharge conduit.

10. In a sample injector having solvent introduction means, metering means with a bore, a solvent inlet port connected to said bore, a piston movable in said bore, and also having an inlet/outlet conduit in fluid communication with said bore, and a discharge conduit, said discharge conduit being connectable to said inlet/outlet conduit at one end and being in fluid communication with a chromatographic column at the other end, a method for injecting liquid sample onto a chromatographic column comprising the steps of:

aspirating a first liquid sample through said inlet/outlet conduit toward said bore by at least partially withdrawing said piston;

connecting said inlet/outlet conduit to said discharge conduit;

with said piston at least partially withdrawn, transporting solvent through said solvent inlet port from said solvent inlet means so that solvent travels through said metering means, said inlet/outlet conduit, and said discharge conduit to said column;

whereby said first liquid sample is transported to said column by solvent and whereby said metering means is flushed of said first liquid sample.

11. A method as recited in claim 10 further comprising the following steps enacted prior to sample aspiration:

pumping a solvent onto said column through said metering means, said inlet/outlet conduit, and said discharge conduit so that solvent fills air spaces along the flow path;

stopping the flow of solvent through said solvent inlet port;

connecting said inlet/outlet conduit to a waste disposal conduit, said waste disposal conduit being in fluid communication with a waste container;

expelling solvent remaining in said bore by at least partially inserting said piston, so that solvent moves from said bore toward said waste container; and disconnecting said inlet/outlet conduit from said waste disposal conduit;

whereby said first liquid sample is transported to said column by solvent free of air trapped in said flow path.

12. A method as recited in claim 11 further comprising the steps of:

directing said flow of solvent to said column when said flow of solvent is stopped through said solvent inlet port;

whereby solvent transport through said column can be maintained concurrently with sample aspiration.

* * * * *